(12) United States Patent
Cook

(10) Patent No.: US 6,172,208 B1
(45) Date of Patent: Jan. 9, 2001

(54) OLIGONUCLEOTIDES MODIFIED WITH CONJUGATE GROUPS

(75) Inventor: Alan Frederick Cook, Cedar Grove, NJ (US)

(73) Assignee: Genzyme Corporation, Framingham, MA (US)

(*) Notice: Under 35 U.S.C. 154(b), the term of this patent shall be extended for 0 days.

(21) Appl. No.: 07/908,376

(22) Filed: Jul. 6, 1992

(51) Int. Cl.$^7$ ...................................................... C07H 21/04
(52) U.S. Cl. ...................... 536/23.1; 536/24.3; 536/24.5; 514/44
(58) Field of Search ................................ 536/23.1, 24.3, 536/24.5; 514/44

(56) References Cited

U.S. PATENT DOCUMENTS 4,904,582  2/1990  Tullis ........................................ 435/6

FOREIGN PATENT DOCUMENTS 9106556  5/1991  (WO).
9110671  7/1991  (WO).

OTHER PUBLICATIONS

Lemaitre et al., *Proc. Natl. Acad. Sci. USA* 84, 648–652 (1987).*
Vestweber & Schatz, *Nature* 338, 170–172 (1989).*
Leamon & Low, *Proc. Natl. Acad. Sci. USA* 88, 5572–5576 (1991).*
Hoflack & Kornfeld, *J. Biol. Chem.* 260(22), 12008–14 (1985).*
Uhlmann, et al., Chemical Reviews, vol. 90, No. 4, pp. 544–584 (Jun. 1990).

* cited by examiner

*Primary Examiner*—Kenneth R. Horlick
(74) *Attorney, Agent, or Firm*—Elliot M. Olstein; Raymond J. Lillie

(57) ABSTRACT

An oligonucleotide wherein at least one nucleotide unit of the oligonucleotide is conjugated with a moiety selected from the group consisting of: (a) amino acids; (b) dipeptide mimics; (c) sugars; (d) sugar phosphates; (e) neurotransmitters; (f) poly-hydroxypropylmethacrylamide; (g) dextrans; (h) polymaleic anhydride; (i) cyclodextrins; (j) starches; and (k) polyethyleneimine. The oligonucleotides may be employed for binding to an RNA, and DNA, a protein, or a peptide to inhibit or prevent gene transcription or gene expression, to inhibit or stimulate the activities of target molecules, or the oligonucleotides may be employed as diagnostic probes for determining the presence of specific DNA or RNA sequences or proteins.

5 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 15 bases
      (B) TYPE: nucleic acid
      (C) STRANDEDNESS: single
      (D) TOPOLOGY: linear (ii) MOLECULE TYPE: oligonucleotide (ix) FEATURE:
      (D) OTHER INFORMATION: N is any purine or pyrimidine base.

(xi) SEQUENCE DESCRIPTION: SEQ ID NO:1:

GGTACANNNT GTTCT                                                           15

(2) INFORMATION FOR SEQ ID NO:2:

(i) SEQUENCE CHARACTERISTICS:
      (A) LENGTH: 15 bases
      (B) TYPE: nucleic acid
      (C) STRANDEDNESS: single
      (D) TOPOLOGY: linear (ii) MOLECULE TYPE: oligonucleotide (ix) FEATURE:
      (D) OTHER INFORMATION: N is any purine or pyrimidine base.

(xi) SEQUENCE DESCRIPTION: SEQ ID NO:2:

GGTTGGNNNG GTTGG                                                           15

OLIGONUCLEOTIDES MODIFIED WITH CONJUGATE GROUPS

This invention relates to oligonucleotides which may bind to a DNA, and RNA, a protein, or a polypeptide, for use as a therapeutic agent or as a diagnostic probe. More particularly, this invention relates to oligonucleotides wherein at least one nucleotide unit of the oligonucleotide includes a conjugate moiety.

Oligonucleotides may be of value as therapeutic agents for the treatment of a wide variety of diseases. They offer the potential for a high degree of specificity by virtue of their capability for interaction with target macromolecules. Natural oligonucleotides, however, are relatively ineffective as therapeutic agents due to their poor penetrability into the cell, and their rapid degradation by enzymes. Therefore, relatively high concentrations of natural oligos are needed in order to achieve a therapeutic effect.

Applicants have found that the attachment of specific classes of conjugate groups to oligonucleotides improves their uptake into the cell, improves their stability, or both. Conjugate groups employed in the present invention, which include amino acids, dipeptide mimics, sugars, sugar phosphates, and neurotransmitters or analogues thereof, have been shown to be transported into the cell by specific transporter systems. These transporters can be used to improve the uptake of oligonucleotide conjugates into the cell, and, depending upon the site of attachment, can also prevent or reduce degradation.

Hydrophilic polymer conjugate groups which may be employed in the present invention, and which include polyhydroxypropylmethacrylamide, dextrans, polymaleic anhydride, cyclodextrins, starches, and polyethyleneimine, may be used to reduce or prevent degradation of the oligonucleotide by blocking access of the conjugate to the enzymes which degrade oligonucleotides.

The scientific literature contains descriptions of certain conjugate groups attached to oligonucleotides.

Conjugates with polylysine have been described by Lemaitre, et al., *Proc. Natl. Acad. Sci. USA*, Vol. 84, pgs. 648–562 (1987), and shown to be more active in cell culture than their unmodified counterparts. Polylysine, however, is not a preferred molecule for conjugation due to its relatively high toxicity. Amphiphilic oligonucleotide conjugates with polyethylene glycol have been described by Tullis in U.S. Pat. No. 4,904,582, and conjugates with cholesterol have been reported by Letsinger et al., (Abstracts, Conference on Nucleic Acid Therapeutics, Clearwater, Fl., (1991)). Many more conjugates have been synthesized for diagnostic applications. In these cases the molecule conjugated to the oligonucleotide acts as a reporter or signaling group, such as, for example, oligonucleotides attached to fluorescent groups which enable the duplex to be detached visually, biotin conjugates which can be detected after capture by streptavidin attached to a signaling group, or enzyme conjugates which can directly generate a signal upon addition of a suitable substrate. Several reviews on modified oligonucleotides, including conjugates have been published; see for example, Uhlmann and Peyman, *Chemical Reviews*, Vol. 90, pgs. 543–584 (1990), and Goodchild, *Bioconjugate Chemistry*, Vol. 1, pgs 165–187 (1990).

In accordance with an aspect of the present invention, there is provided an oligonucleotide wherein at least one nucleotide unit of the oligonucleotide is conjugated with a moiety selected from the group consisting of (a) amino acids; (b) dipeptide mimics; (c) sugars; (d) sugar phosphates; (e) neurotransmitters; (f) polyhydroxypropylmethacrylamide; (g) dextrans; (h) polymaleic anhydride; (i) cyclodextrins; (j) starches; and (k) polyethyleneimine.

The term "oligonucleotide" as used herein means that the oligonucleotide may be a ribonucleotide, deoxyribonucleotide, or a mixed ribonucleotide/deoxyribo nucleotide; i.e., the oligonucleotide may include ribose or deoxyribose sugars or a mixture of both. Alternatively, the oligonucleotide may include other 5-carbon or 6-carbon sugars, such as, for example, arabiose, xylose, glucose, galactose, or deoxy derivative thereof or any mixture of sugars.

The phosphorus-containing moieties of the oligonucleotides of the present invention may be modified or unmodified. The pohosphorus-containing moiety may be, for example, a phosphate, phosphonate, alkylphosphonate, aminoalkyl phosphonate, thiophosphonate, phosphoramidate, phosphorodiamidate, phosphorothioate, phosphorothionate, phosphorothiolate, phosphoramidothiolate, and phosphorimidate. It is to be understood, however, that the scope of the present invention is not to be limited to any specific phosphorus moiety or moieties. Also, the phosphorus moiety may be modified with a cationic, anionic, or sqitterionic moiety. The oligonucleotides may also contain backbone linkages which do not contain phosphorus, such as carbonates, carboxymehtyl esters, acetamidates, carbamates, acetals, and the like.

The oligonucleotides also include any natural or unnatural, substituted or unsubstituted, purine or pyrimidine base. Such purine and pyrimidine bases include, but are not limited to, natural purines and pyrimidines such as adenine, cytosine, thymine, guanine, uracil, or other purines and pyrimidines, such as isocytosine, 6-methyluracil, 4,6-dihydroxyprimidine, hypoxanthine, xanthine, 2,6-diaminopurine, 5-azactosine, 5-methyl cystosine, and the like.

In general, the oligonucleotide includes at least two, preferably at least 5, and most preferably from 5to 30 nucleotide units.

In one embodiment, the at least one nucleotide unit which includes the conjugate moiety is the 3' terminal nucleotide unit. In another embodiment, the at lest one nucleotide unit is the 5' terminal nucleotide unit.

Alternatively, the at least one nucleotide unit which includes a conjugate moiety as hereinabove described is one or more nucleotide units at the 3' end and/or the 5' end of the oligonucleotide. In yet another embodiment, the at least one nucleotide unit may alternate with nucleotide units which are unsubstituted (i.e., which do not include a conjugate moiety). In another embodiment, all of the nucleotide units include a conjugate moiety.

The conjugate moiety may be attached to the oligonucleotide at the purine or pyrimidine base, at the phosphate group, or to the sugar.

When the conjugate moiety is attached to the base, it is preferably attached at certain positions of the base, depending upon the base to which the moiety is attached. When the moiety is attached to adenine, it may be attached at the C2, N6, or C8 positions. When the moiety is attached to guanine, it may be attached at the N2 or C8 positions. When the moiety is attached to cytosine, it may be attached at the C5 or N4 positions. When the moiety is attached to thymine or uracil, it may be attached at the C5 position.

The moiety may be attached to a phosphate group at the 5' end, at an internal position, or at the 3' end of the oligonucleotide. The moiety may be attached to the 5' end of the oligonucleotide via an —$NH_2$—$(CH_2)_6$— linker (such as Aminolink II, for example), via a phosphodiester linkage, or via other linkers. A wide variety of linker groups may be employed, depending upon the nature of the nucleotide unit, the moiety, and whether the linker group is present during the synthesis of the oligonucleotide. The linker group may be a single atom, or a functional group. Examples of linkers include, but are not limited to —NH—, or amino groups, sulfur atoms, and polyvalent functional groups.

In another embodiment, the linking group is derived from a polyvalent functional group having at least one atom, and not more than about 60 atoms other than hydrogen, preferably not more than about 30 atoms other than hydrogen. The linker group in general has up to about 30 carbon atoms, preferably not more than about 20 carbon atoms, and up to about 10 heteroatoms, preferably up to about 6 heteroatoms, and in particular such heteroatoms may be oxygen, sulfur, nitrogen, or phosphorus. Representative examples of linker groups include, but are not limited to —CO—(CH$_2$)$_n$—NH—;
—CO—(CH$_2$)$_n$—CO$_{13}$;

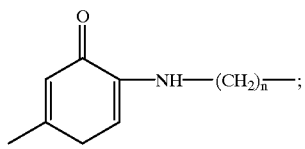

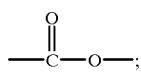

—(CH$_2$)$_n$—NH—; —CO—; —CO—CH$_2$—CH$_2$—S—S—;
—CH$_2$—CH$_2$NHCO(CH$_2$)$_n$ CONH—; —CH$_2$CH$_2$—NH—
Q—(CH$_2$)$_n$NH—, wherein Q is 2,5-quinondiyl;

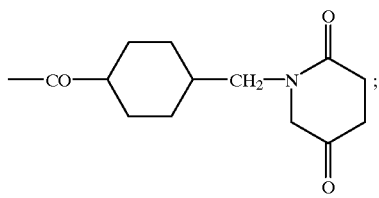

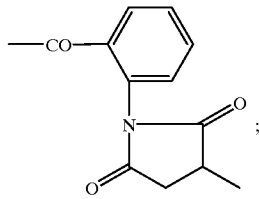

In the above structures, n is from 1 to 20, preferably from 2 to 12, and more preferably 6.

The moiety may be attached at internal positions to a phosphate group via a P—N linker, a P—S linker, or a P—O linker. The moiety also may be attached at the 3' end to a phosphate group via a phosphodiester linkage.

When the moiety is attached to a sugar of an oligonucleotide, the moiety may be attached at the 2'-position; at the hydroxy group of the 3' -end or the 5' end; via a 3'-terminal ribose dialdehyde; at the 1'-position; or by using a 3'-terminal amino linker, such as, for example, a 3'-amino modified controlled pore glass (C3 CPG) which is commercially available from Glen Research, Serling, Va.

Although the moieties may be attached to the oligonucleotides at the various positions and by the various means hereinabove described, it is to be understood that the scope of the present invention is not to be limited to such means of attachment.

Amino acids which may be conjugated to the at least one nucleotide unit include, but are not limited to, alanine, methionine, leucine, isoleucine, and lysine. The amino acid may be attached to the at least one nucleotide unit by the acid functionality, the amino group, or by the side chain.

In one embodiment, an active ester derivative of fluorenyl-methoxycarbonyl (F-moc)-alanine is reacted with an oligonucelotide having a 5'-amino group to provide an intermediate which, after deprotection by treatment with base, provides a conjugate with the amino acid attached to the oligonucleotide via its carboxyl group.

In another embodiment, reaction of an oligonucleotide possessing a 5'-amino group with a bifunctional linker arm reagent such as disuccinimidyl suberate (DSS) provides an activated intermediate which may react with the amino groups of an amino acid to provide the desired conjugate.

Other crosslinking agents with shorter or longer linker arms may be used in place of discuccinimidyl suberate. Alternatively, active esters can be reacted with the oligonucleotide 2'-hydroxyl group or a 2'-thiol group to give conjugates linked via ester or thioester linkages, respectivley. Attachment to the side chain of an amino acid depends upon the nature of the amino acid because the side chains differ widely. Attachment to acidic or basic side chains can be carried out by methods similar to those described for the carboxyl and amino groups, whereas attachment to hydrocarbon side chains necessitates introduction of new attachment sites. Both D- and L-amino acids can be attached by these methods.

Dipeptide mimics which may be conjugated to the at least one nucleotide unit include, but are not limited to, amino ethyl glycine, and cephalosporins. Cephalosporins which may be employed include, but are not limited to, cephalexin, cephradine, cefaclor, cefadroxil, cefazolin, and cefotiam.

The dipeptide mimic amino ethyl glycine may be reacted with trifluoroacetic anydride, or (CF$_3$CO)$_2$O, and the reaction product is then reacted with N-hydroxysuccinimide (NHS) and dicyclohexyl carbodiimide (CDD). This product is then reacted with an oligonucleotide having an aminoalkyl linker such as an NH$_2$—(CH$_2$)$_6$— linker attached to the 5'-phosphate moiety. The amino ethyl glycine attaches to the —NH$_2$— group of the linker via the carboxyl group. After conjugation, the trifluoroacetyl protecting groups are removed by treatment with dilute ammonium hydroxide.

Aminocephalosporins have been shown to be transported into cells via the dipeptide transport system of intestinal brush border membranes as was describe din the *Journal of Biological Chemistry*, Volume 261, pgs. 14130–14134 (1986), and thus can be considered as dipeptide mimics. These can be attached to oligonucleotides to produce conjugates which can be taken up by dipeptide transport systems and thus be internalized more efficiently. These molecules possess amino and carboxyl groups, both of which can be used as attachment sites for conjugation using methods outlined above. Attachment to the amino group of the cephalosporin can be accomplished by using a crosslinking agent which forms amide bonds with both the cephalosporin and with an oligonucleotide amino group. Attachment via the carboxyl group can be accomplished by activation to give an active ester which can be reacted directly with an oligonucleotide amino group, or reacted with an amino group attached to the 5' or 3'-position via a linker arm. Alternatively, such active esters can be reacted with the oligonucleotide 2'-hydroxyl group or the 2'-thiol group to give conjugates linked via ester or thioester linkages, respectivley. In addition, thee compounds have other ring substituent groups which can be used as linkage sites without interfering with the amino and carboxyl functionalities.

Dipeptide mimics such as amino ethyl glycine also possess amino and carboxyl groups, both of which can be used for attachment. Attachment via the amino group can be accomplished by using a crosslinking agent such as disuccinimidyl suberate, which forms amide bonds with both the dipeptide mimic and with a 2'-oligonucleotide amino group. Other crosslinking agents can also be employed in place of disuccinimidyl suberate. Attachment via the carboxyl group can be accomplished by activation using an active ester as is hereinabove described with respect to amino acids. Such esters could be reacted directly with a 5'-amino group on the oligonucleotide, or reacted with an amino group attached to the 5'-position via a linker arm. Alternatively, such active esters can be reacted with the 2'-hydroxyl group or a 2'-thiol group to give conjugates linked via ester or thioester linkages, respectivley.

Sugars which may be conjugated to the at least one nucleotide unit include, but are not limited to, 5-carbon sugars and 6-carbon sugars. 5-carbon sugars which may be employed include, but are not limited to, ribose, arabionse, xylose, and lyxose. 6-carbon sugars include, but are not limited to, glucose, galactose, mannose, allose, glucose, idose, talose, and altrose. Preferred sugars are glucose, galactose, and mannose.

Sugars have several hydroxyl groups which can be used for attachment to oligonucleotides. In one embodiment, one may react a partially protected sugar derivative such as 1,2,34-tetraacetyl-D-glucopyranose with a 5'-phosphorylated oligonucleotide using a condensing agent such as dicyclohexylcarbodiimide or tri-isopropylbenzenesulfonyl chloride. Another approach is to use a crosslinking agent to attach a linker arm bearing an active ester group to a 5'-oligonucleotide amino group. This active ester would be capable of reacting with a hydroxyl group of the sugar to give an ester linkage. Yet another approach is to couple an active ester of an acid derivative of a sugar to an oligonucleotide amino group to produce an amide linkage. Still another approach is to react a sugar isothiocyanate such as 2,3,4,6-tetraacetyl-D-glucopyranose-1-isothiocyanate with a 5' or 3'-oligonucleotide amino group to give a thiourea linkage.

In another embodiment, the sugar may be protected with one or more acetyl groups and a phosphate group. The protected sugar is then reacted with a partially protected oligonucleotide attached to controlled pore glass as synthesized by using a DNA synthesizer machine. The protected sugar and the protected oligonucleotide are reacted in the presence of a coupling agent, which may be dicyclohexyl-carbodiimide or mesitylenesulfonyl chloride to form an oligonucleotide to which is attached a sugar through attachment of the sugar to the phosphate group. The protecting groups are subsequently removed using ammonium hydroxide.

Sugar phosphates can be used as conjugate groups to enhance the delivery of oligonucleotides into cells. Distler et al., in the *Journal of Biological Chemistry,* Vol. 266, pages 21687–92 (1991) have shown that oligosaccharides containing a terminal mannose-6-phosphate residue inhibited the binding of beta-galactosidase to mannose-6-phosphate cell surface receptors from bovine testis, with the di- and trisaccharides being more effective inhibitors than the monosaccharide mannose-6-phosphate. The nature of the penultimate glycosidic linkages of the oligosaccharides played little or no role in the inhibition of binding. Tomoda et al., in *Carbonhydrate Research,* Vol. 213, pages 37–46 (1991) prepared conjugates of mannose-6-phoshpate and oligosaccharides thereof with bovine serum albumin, and showed that these conjugates bound to the mannose-6-phosphate receptor from rabbit alveolar macrophages.

Sugar phosphates which may be attached to the at least one nucleotide unit include, but are not limited to, manosaccharides such as mannose-6-phosphate, glucose-6-phosphate, galactose-6-phosphate, mannose-1-phosphate, glucose-1-phosphate and galactose-1-phosphate, disaccharides such as 6-O-phosphoryl-α-D-mannopyranosyl-(1-2)-D-mannopyranose, 6-O-phosphoryl-α-D-mannopyranosyl-(1-3)-mannopyranose, 6-O-phosphoryl-α-D-mannopyranosyl-(1-6)-D-mannopyranose, trisaccharides such as 6-O-phosphoryl-α-D-mannopyranosyl-(1-2)-D-mannopyranose-(1-2)-D-mannopyranose, and higher linear or branched oligosaccharides such as pentamannose-6-phosphate.

Sugar phosphates may be attached to oligonucleotides by a reductive amination procedure similar to the method used by Baba, et al., in *Carbonhydrate Research,* Vol. 177, pages 163–172 (1988) for the conjugation of pentamannosyl-6-phosphate to bovine serum albumin, or by formation of a glycoside possessing a linker arm which can be attached to an oligonucleotide.

Sugar phosphates may be attached to oligonucleotides by condensation reactions via the phosphate group. For example, reaction of 1,2,3,4-tetraacetyl-glucose-6-phosphate with the 5'-terminal amino group of an oligonucleotide using a condensing agent such as tri-isopropylbenzenesulfonyl tetrazolide will produce a conjugate in which the sugar phosphate is linked to the oligonucleotide via a phosphoramidate linkage. Alternatively, 1,2,3,4-tetraacetyl=glucose-6-phosphate can be coupled to the 2'-hydroxyl group of a ribonucleotide using the same condensing agent to produce a conjugate linked via a phosphodiester.

Neurotransmitters which may be conjugated to the at least one nucleotide unit of the oligonucleotide include, but are not limited to, dopamine, acetylcholine, epinephrine, norepinephrine, and serotonin.

Acetylcholine may be attached to the oligonucleotide by reacting choline, which has the following structural formula:

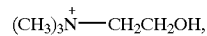

with $(BrCH_2-CO)_2O$ to form the following protected compound:

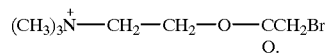

This compound is reacted with an oligonucleotide having a thiol group at the 5' end of the oligonucleotide to form an oligonucleotide to which acetylcholine is conjugated through a —CO—CH$_2$—S-group.

Norepinephrine, dopamine, and serotonin, each of which have an amino group, may be conjugated to an oligonucleotide by reacting the amino group with an activated oligonucleotide. Such reaction of the amino group with the activated oligonucleotide results in conjugation of the neurotransmitter with the oligonucleotide.

Polymers which may be conjugated with the oligonucleotides in accordance with the present invention include polyamines, cyclodextrins, dextrans, polyethyleneimine, polymaleic anhydride, poly-hydroxypropylmethacrylamide (HPMA), and starches.

Polyamines which may be conjugated to the at least one nucleotide unit include the naturally occurring cationic compounds sperimine and spermidine. It is to be understood, however, that the scope of the present invention is not to be limited to these specific polyamines. Polyamines can be attached to the at least one nucleotide unit by methods which include, but are not restricted to, the following:

1. Reaction of the polyamine with an oligonucleotide having a 5'- or 3'-phosphomonoester group in the presence of DCC to produce a conjugate linked by a phosphoramidate linkage.

2. Reaction of the polyamine with an oligonucleotide H-phosphonate to produce a conjugate in which the polyamine is attached to the pohosphate backbone.

3. Treatment of an oligonucleotide containing a 3'-terminal ribonucleotide with periodate to give a dialdehyde which is then reacted with the polyamine to form a conjugate attached via a morpholine ring.

In one embodiment, dextran is conjugated with the oligonucelotide by reacting an activated dextran with a protected oligonucleotide. Dextran may be activated by reacting dextran with Br—(CH$_2$)$_5$—COOH in the presence of sodium hydroxide to form dextran-O—(CH$_2$)$_5$—COOH, which is then reacted in the presence of dimethylformamide, hexamethylphosphoramide (HMPA), pyridine, and DCC to form the active ester derivative:

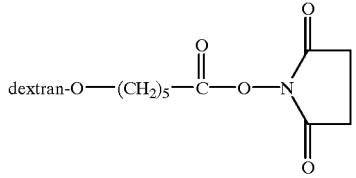

The preparation of the derivative is described in Pietta, et al., *Preparative Biochemistry*, Vol. 14, pgs. 313–329 (1984). Other methods for the derivatization of dextran are described in Schact, *Industrial Polysaccharides: Genetic Engineering, Structure/Property Relations and Applications*, Yalpani, ed., pags. 389–400 (1987), and in Yalpani, et al., *Journal of Polymer Science: Polymer Chemistry Edition*, Vol. 23, pgs. 1395–1405 (1985).

This active ester derivative of dextran is reacted with an oligonucleotide containing an amino group in the presence of sodium phosphate buffer (pH 8.25) to form an oligonucelotide conjugated with dextran.

Poly HPMA may be conjugated with an oligonucelotide by reacting a copolymer of HPMA and the 4-nitrophenyl ester of N-methacryloylaminocaproic acid with an oligonucleotide protected with an amino group.

The 4-nitrophenyl ester of N-methacryloylaminocaproic acid is prepared by reacting methacryloyl chloride with 6-aminohexanoic acid in the presence of sodium hydroxide, water, and hdyrochloric acid to form:

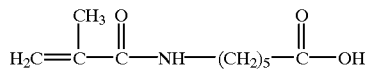

This is reacted with 4-nitrophenol in the presence of DCC and dimethylformamide to form the 4-nitrophenyl ester of N-methacryloylaminoacaproic acid, which has the following structure:

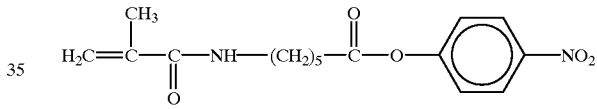

HPMA monomer is reacted with the 4-nitrophenyl ester of N-methacryloylamiocaproic acid in the presence of 2,2'-azobisisobutyronitrile (AIBN) and acetone at 50° C. to form a copolymer having the following structure:

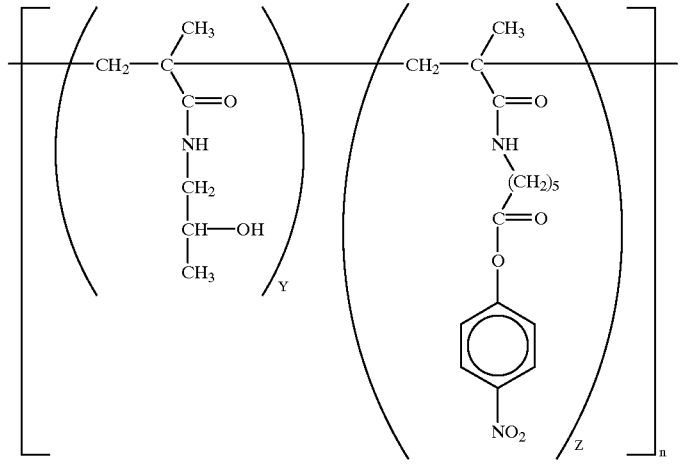

Y is from about 10 to about 50, Z is at least 1 (preferably 1), and n is from 1 to 10.

The details of the formation of this copolymer are described by Kopecek, et al., in the *Journal of Polymer Science,* Polymer Symposium 66, pgs. 15–32 (1979).

This copolymer is than reacted with an oligonucleotide protected with an amino group to form an oligonucleotide conjugate having the following structure:

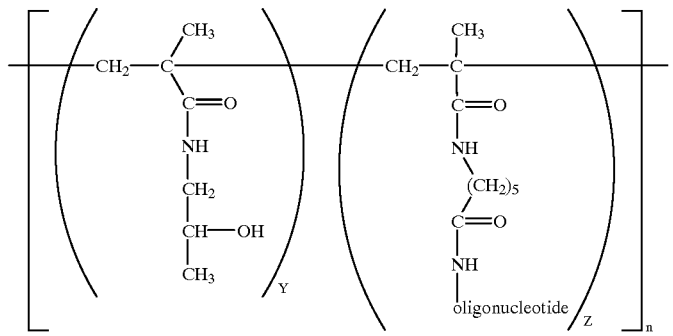

Y, Z and n are as hereinabove described.

Because cyclodextrins and starches possess similar or identical carboxyhdrate monomer units to those contained in dextran, the same methods for the conjugation to oligonucleotides can be employed. In addition, Tabushi, et al., in the *Journal of the American Chemical Society,* Vol. 98, pg. 7855 (1976) have described a disulfonate derivative of β- cyclodextrin which can be reacted with a diamine to give a β-cyclodextrin-diamine adduct. This latter derivative can be coupled to an oligonucleotide in a variety of ways to give a β-cyclodextrin-oligonucleotide conjugate. For example, reaction of the β- cyclodextrin-diamine adduct with an oligonucleotide containing a 5'- phosphate group in the presence of a carbodiimide coupling agent would produce a 5'- linked conjugate.

Polyethyleneimine (PEI) can be conjugated to oligonucleotides in a variety of ways. For examples, reaction of PEI with an oligonucleotide containing a 5'-phosphate group in the presence of a carbodiimide coupling agent would produce a PEI-oligonucleotide conjugated at the 5'-position.

The oligonucleotides of the present invention may be employed to bind to RNA sequences by Watson-Crick hybridization, and thereby block RNA processing or translation. For example, the oligonucleotides of the present invention may be employed as "antisense" complements to target sequences of mRNA in order to effect translation arrest and selectively regulate protein production.

The oligonucleotides of the present invention may be employed to bind double-standard DNA to form triplexes, or triple helices. Such triplexes inhibit the replication or transcription of DNA, thereby disrupting gene replication or transcription. Such triplexes may also protect DNA binding sites from the action of enzymes such as DNA methylases.

The oligonucleotides of the present invention may be employed to bind specifically to target proteins, or to selected regions of target proteins so as to block function or to restore functions that had been lost by a protein as a result of mutation. For example, the oligonucleotides of the present invention may be used to block the interaction between a receptor and its ligand(s) or to interfere with the binding of an enzyme or its substrate or cofactor or to interfere otherwise with the catalytic action of an enzyme. Conversely, the oligonucleotides of the present invention may be employed to restore lost function to a mutated protein, for example, by eliciting conformational alteration of such a protein through formation of a complex with that protein.

The RNA, DNA, or protein target of interest, to which the oligonucleotide binds, may be present in or on a porkaryotic or eukaryotic cell, a virus, a normal cell, or a neoplastic cell, in a bodily fluid or in stool. The target nucleic acids or proteins may be of plasmid, viral, chromosomal, mitochondrial or plastid origin. The target sequences may include DNA or RNA open reading frames encoding proteins, mRNA, ribosomal RNA, snRNA, hnRNA, introns, or untranslated 5'- and 3'-sequences flanking DNA or RNA open reading frames. The modified oligonucleotide may therefore be involved in inhibiting production or function of a particular gene by inhibiting the expression of a repressor, enhancing or promoting the function of a particular mutated or modified protein by eliciting a conformational change in that protein, or the modified oligonucleotide may be involved in reducing the proliferation of viruses, microorganisms or neoplastic cells.

The oligonucleotides may be used in vitro or in vivo for modifying the phenotype of cells, or for limiting the proliferation of pathogens such as viruses, bacteria, portists, Mycoplasma spcies, Chlamydia or the like, or for killing or interfering with the growth of neoplastic cells or specific classes of normal cells. Thus, the oligonucleotides may be administered to a host subject in a diseased state to inhibit the transcription and/or expression of the native genes of a target cell, or to inhibit function of a protein in that cell. Therefore, the oligonucleotides may be used for protection from, or treatment of, a variety of pathogens in a host, such as, for example, enterotoxigenic bacteria, Pneumococci, Neisseria organisms, Giardia organisms, Entamoebas, neoplastic cells, such as carcinoma cells, sarcoma cells, and lymphoma cells; specific B-cells; specific T-cells, such as helper cells, suppressor cells, cytotoxic T-lymphocytes (CTL), natural killer (NK) cells, etc.

The oligonucleotides may be selected so as to be capable of interfering with transcription product maturation or production of proteins by any of the mechanisms involved with the binding of the subject composition to its target sequence. These mechanism may include interference with processing, inhibition of transport across the nuclear membrane, cleavage by endonucleases, or the like.

The oligonucleotides may be complementary to such sequences as sequences expressing growth factors, lymphokines, immunoglobulins, T-cell receptor sites, MHC antigens, DNA or RNA polymerases, antibiotic resistance, multiple drug resistance (mdr), genes involved with metabolic processes, in the formation of amino acids, nucleic acids, or the like, DHFR, etc. as well as introns or flanking sequences associated with the open reading frames.

The following table is illustrative of some additional applications of the subject compositions.

| Area of Application | Specific Application Targets |
|---|---|
| Infectious Diseases: | |
| Antivirals, Human | HIV, HSV, CMV, HPV, VZV infections |
| Antivirals, Animal | Chicken Infectious Bronchitis Pig Transmissible Gastroenteritis Virus infections |
| Antibacterial, Human | Drug Resistance Plasmids |
| Antiparasitic Agents | Malaria Sleeping Sickness (Trypanosomes) |
| Cancer | |
| Direct Anti-Tumor Agents | Oncogenes and their products |
| Adjunctive Therapy | Drug Resistance genes and their products |
| Auto Immune Diseases | |
| T-cell receptors | Rheumatoid Arthritis Type I Diabetes Systemic Lupus Multiple sclerosis |
| Organ Transplants | OKT3 cells causing GVHD |

The oligonucleotides of the present invention may be employed for binding to target molecules, such as, for example, proteins including, but not limited to, ligands, receptors, and or enzymes, whereby such oligonucleotides inhibit the activity of the target molecules, or restore activity lost through mutation or modification of the target molecules.

The oligonucleotides of the present invention are administered in an effective binding amount to an RNA, a DNA, a protein, road peptide. Preferably, the oligonucleotides are administered to a host, such as a human or non-human animal host, so as to obtain a concentration of oligonucelotide in the blood of from about 0.1 to about 100 μmole/l. It is also contemplated that the oligonucleotides may be administered in vitro or ex vivo as well as in vivo.

The oligonucleotides may be administered in conjunction with an acceptable pharmaceutical carrier as a pharmaceutical composition. Such pharmaceutical compositions may contain suitable excipients and auxiliaries which facilitate processing of the active compounds into preparations which can be used pharmaceutically. Such oligonucleotides may be administered by intramuscular, intraperitoneal, intraveneous, or subdermal injection in a suitable solution. Preferably, the preparations particularly those which can be administered orally and which can be used for the preferred type of administration, such as tablets, dragees and capsules, and preparations which can be administered rectally, such as suppositories, as well as suitable solutions for administration parentally or orally, and compositions which can be administered buccally or sublingually, including inclusion compounds, contain from about 0.1 to 99 percent by weight of active ingredients, together with the excipient. It is also contemplated that the oligonucleotides may be administered topically.

The pharmaceutical preparations of the present invention are manufactured in a manner which is itself well known in the art. For example, the pharmaceutical preparations may be made by means of conventional mixing, granulating, degree-making, dissolving or lyophilizing processes. The process to be used will depend ultimately on the physical properties of the active ingredient used.

Suitable excipients are, in particular, fillers such as sugar, for example, lactose or sucrose, mannitol or sorbiotl, cellulose preparations and/or calcium phosphates, for example, tricalcium phosphate or calcium hydrogen phosphate, as well as binders such as starch or paste, using, for example, maize starch, wheat starch, rice starch, potato starch, gelatin, gum tragacanth, methylc ellulose, hydroxypropylmethylcellulose, sodium carboxypropylmethyl-cellulose, sodium carboxymethylcellulose, and/or polyvinyl pyrrolidone. If desired, disintegrating agents may be added, such as the above-mentioned starches as well as carboxymethyl-starch, cross-linked polyvinyl pyrrolidone, agar, or aliginic acid or a salt thereof, such as sodium aliginate. Auxiliaries are flow-regulating agents and lubricants, such as, for example, silica, talc, stearic acid or salts thereof, such as magnesium stearate or calcium stearate, and/or polyethylene glycol. Dragee cores may be provided with suitable coatings which, if desired, may be resistant to gastric juices. For this purpose, concentrated sugar solutions may be used, which may optionally contain gum arabic, talc polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such a acetylcellulose phthalate or hydroxypropylmethyl-cellulose phthalate, are used. Dyestuffs and pigments may be added to the tablets of dragee coatins, for example, for identification or in order to characterize different combinations of active compound loses.

Other pharmaceutical preparations which can be used orally include push-fit capsules made of gelatin, as well as soft, sealed capsules made of gelatin and a plasticizer such as glycerol or sorbitol. The push-fit capsules can contain the oligonucleotide in the form of granules which may be mixed with fillers such as lactose, binders such as starches, and/or lubricants such as talc or magnesium stearate and, optionally, stablizers. In soft capsules, the active compounds are preferably dissolved or suspended in suitable liquids, such as fatty oils, liquid paraffin, or liquid polyethylene glycols. In addition, stabilizers may be added.

Possible pharmacectical preparations which can be used rectally include, for example, suppositories, which consist of a combination of the active compounds with a suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble or water-dispersible form. In addition, suspensions of the active compounds as appropriate oil injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension including, for example, sodium carboxymethyl cellulose, sorbitor and/or dextran. Optionally, the suspension may also contain stabilizers.

Additionally, the compounds of the present invention may also be administered encapsulated in liposomes, wherein the active ingredient is contained either dispersed or variously present in corpuscles consisting of aqueious concentric layers adherent to lipidic layers. The active ingredient, depending upon its solubility, may be present both in the aquious layer, in the lipidic layer, or in what is generally termed a liposomic suspension. The hydrophobic layer, generally but not exclusively, comprises phospholipids such as lecithin and sphingomycelin, steroids such as cholesterol, surfactants such as dicetylphosphate, stearylamine, or phsophatidic acid, and/or other materials of a hydrophobic nature. The diameters of the liposomes generally range from about 15 nm to about 5 microns.

The oligonucleotide conjugates of the present invention may also be employed as diagnostic probes. In this approach the conjugate group serves as a radioactive or nonradioactive reporter group for the detection of nucleic acid sequences of interest. In one embodiment, the DNA-containing sample to be analyzed is immobilized on an inert solid support such as a nitrocellulose membrane and then annealed with the oligonucleotide conjugate. This annealing procedure allows the conjugated oligonucleotide to bind to the DNA provided that the base sequences are complementary to each other. After a series of washing steps the duplex of the oligonucleotide conjugate with the DNA is exposed to a complex of an antibody to the conjugate group attached to an enzyme such as alkaline phosphatase. After a further series of washing steps, the DNA-antibody-enzyme complex is detected by exposure to a chromogenic substrate which generates a purple-blue color in the area of the bound complex.

In another embodiment, the conjugate group on the oligonucleotide may be a carbonhydrate and the modified oligonucleotide bound to the complementary DAN can be detected by complex formation with a lectin specific for the carbohydrate conjugate group, such lectin subsequently being complexed with an antibody attached to an enzyme such as alkaline phosphatase.

Several other conjugate groups have ben used in this manner. For example, oligonucleotide diagnostic probes have been prepared by attachment of digoxigenin to the 5-position of pyrimidine bases are reported by Muhlegger et al. in *Nucleosides and Nucleotides*, Vol. 8, pages 1161–1163 (1989), and conjugates of the 2,4-dinitrophenyl group have been reported by Vincent et al. in *Nucleic Acids Research*, Volume 10, pages 6787–6796 (1982).

The oligonucleotide conjugates can also be used as diagnostic probes to interact with RNA's in a sample provide that the target RNA has a sequence complementary to the sequence of the conjugated oligonucleotide. If both DNA and RNA are present in the sample and it is desired to measure only DNA, the sample can be treated with RNase prior to addition of the oligonucleotide conjugate. If it is desired to measure only RNA, the sample can be treated with DNase prior to addition of the oligonucleotide conjugate. The oligonucleoitde conjugates can also be used as diagnostic probes to interact with proteins in a sample provided that the target protein binds tightly or specifically to the conjugated oligonucleotide because of the sequence of the conjugated oligonucleotide. For example, the glucocorticoid receptor protein has been demonstrated to bind with high affinity to the sequence GGTACAN$_3$TGTTCT, (SEQ ID NO: 1) wherein N is any purine or pyrimidine base. (R. M. Evans, Science, Vol. 240, pgs. 889 (1988)). A double-stranded oligonucleotide in which one strand is an oligonucleotide conjugate of the present invention could be used as a diagnostic probe to measure glucocorticoid receptor protein in a sample. Other DNA-binding proteins can be similarly measured. Bock et al. (*Nature,* Vol. 355, pages 564–566, (1992) have demonstrated that the protein thrombin binds tightly to DNA oligonucleotides containing the consensus sequence GGTTGG(N$_3$)GGTTGG. (SEQ ID NO: 2) An oligonucleotide of the present invention containing ribonucleotides or deoxyribonucleotides of a given sequence might thus be used to detect a protein which bind that sequence.

The invention will now be described with respect to the following examples; however, the scope of the present invention is not intended to be limited thereby.

EXAMPLE 1

Attachment of Methionine to an Oligonucleotide

A 15-base oligonucleotide was prepared on a DNA synthesizer using standard reagents as supplied by the manufacturer.

Cyanoethyoxy-di-isopropylamin-trifluoroacetylaminohexyloxy-phosphine (Aminolink II) was used for the final coupling step to introduce a linker arm onto the 5'-terminus of the oligonucleotide. The crude oligonucleotide was treated with concentrated ammonium hydroxide for 12 hours at 55° C. to remove the base protecting groups, and the solution was evaporated to dryness. A solution of the 5'-amino oligonucleotide (190 OD$_{260}$ units) in 0.1 M sodium bicarbonate (pH 8.2; 150 µl) was added to an Eppendorf tube containing a solution of the N-hydroxysuccinimide ester of N-fluoroenylmethoxycarbonyl-L-methionine (6.2 mg) in dimethylsulfoxide (300 µl), and the resulting mixture was vortexed for 15 sec. and then incubated at ambient temperature for 7 hours. The product was neutralized by addition of acetic acid to pH 7, stored overnight, and evaporated to dryness. The residue was coevaporated with water (3×25 ml), dissolved in water (6 ml) and lyophilized overnight. The residue was then purified by preparative reversed phase C$_{18}$ HPLC (9×25 cm) using a gradient of 0.1 M triethylammonium acetate (pH 7.1)/acetonitrile as eluent. The fraction containing the desired product was collected, evaporated to dryness and coevaporated with water (3×25 ml). The residue was treated with a solution of morpoholine in water (1:1, 2 ml) for 45 min. at room temp to remove the fluorenylmethoxycarbonyl group, evaporated to dryness and coevaporated with water (3×1 ml) to remove traces of morpholine. The residue was partitioned between water and ethyl acetate (2 ml each) and the aqueous layer was extracted with ethyl acetate (2×2 ml) and lyophilized to dryness. The residue was dissolved in water (1 ml) and converted into the sodium salt by passage through a column of ion exchange resin (Dowex AG 50W-X8, sodium form, 0.7×6 cm). The eluent was collected and evaporated to dryness to give the oligonucleotide-methionine conjugate.

EXAMPLE 2

Attachment of Glucose to a 5'-Amino-oligonucleotide

A solution of the 5'-amino oligonucleotide (100 OD$_{260}$ units) in 0.2 M sodium phosphate (pH 7.0; 70 µl) is added to an Eppendorf tube containing a solution of 2,3,4,6-tetra-O-acetyl-β-D-glucopyransoyl-isothiocyanate (1 mg) in dimethylformamide (30 µl) and the resulting mixture is stirred for 15 seconds and then incubated at ambient temperature for 1 day. The mixture is deprotected with aqueious ammonium hydroxide at room temperature and evaporated to dryness. The residue is dissolved in water, filtered, and purified by reversed phase $C_{18}$ HPLC to give the glucose-oligonucleotide conjugate.

EXAMPLE 3

Synthesis of an Oligonucleotide-Aminoethyl Glycine Conjugate

A solution of aminoethyl glycine in pyridine is treated with trifluoroacetic anhydride at 0° C. For 18 hours. Water is added to the chilled solution, and after 1 hour the mixture is evaporated to dryness and pumped in vacuo overnight to give the N, N-trifluoroacetyl derivative of aminoethyl glycine. This material is dissolved in dimethylformamide and treated with a solution of 5'-amino oligonucleotide in acetate buffer, pH 5 followed by 1-(3-dimethylaminopropyl)-3-ethylcarbodiimide (EDC). After incubation for 18 hours at room temperature, the solution is evaporated to dryness, dissolved in N-ammonium hydroxide, and stored at room temperature overnight. The residue is dissolved in 0.02 M triethylammonium bicarbonate and purified by preparative reversed phase $C_{18}$ HPLC to give the aminoethyl glycine-oligonucleotide conjugate.

EXAMPLE 4

Synthesis of an Oligonucleotide-Cephalosporin Conjugate

The aminocephalosporin Cephalexin (Shionogi and CO.) is dissolved in pyridine and treated with trifluoroacetic anhydride at 0° C. for 18 hours. Water is added to the chilled solution, and after 1 hour the mixture is evaporated to dryness and pumped in vacuo overnight, dissolved in dimethylformamide and treated with a solution of 5'-amino oligonucleotide in acetate buffer, pH 5, followed by addition of EDC. After storage for 18 hours at room temperature, the solution is evaporated to dryness, dissolved in N-ammonium hydroxide, and incubated at room temperature overnight. The residue is filtered, dissolved in 0.02 M triethylammonium bicarbonate and purified by preparative reversed phase $C_{18}$ HPLC to give the aminocephalosporin-oligonucleotide conjugate.

EXAMPLE 5

Attachment of Glucose-6-Phosphate to an Oligonucleotide

A suspension of glucose-6-phosphate, pyridinium salt, in pyridine is treated with stirring at 0° C. with acetic anhydride for 18 hours, and then treated with water for 4 hours. The solvents are removed by evaporation and the residue is dissolved in dimethylformamide and treated with a solution of 5'-amino oligonucleotide in acetate buffer, pH 5 followed by EDC. After incubation for 18 hours at room temperature, the solution is evaporated to dryness, dissolved in 5 N ammonium hdyroxide, and stored at room temperature overnight. This solution is evaporated to dryness, and the residue is dissolved in 0.02 M triethylammonium bicarbonate, filtered, and the filtrate is purified by preparative reverse phase $C_{18}$ HPLC to give the glucose-6-phosphate-oligonucleotide conjugate.

EXAMPLE 6

Preparation of a Neurotransmitter-Oligonucleotide Conjugate

An oligonucleotide is prepared on a DNA synthesizer using standard reagents as supplied by the manufacturer. Cyanoethoxy-di-isopropylamino-trifluoroacetylaminohexyloxy-phosphine (Aminolink II) is used for the final coupling step to introduce a linker arm onto the 5'-terminus of the oligonucleotide. The crude oligonucleotide is treated with concentrated ammonium hydroxide for 12 hours at 55° C. to remove the protecting groups, and the solution is evaporated to dryness. A solution of the 5'-amino oligonucleotide in 0.1 M sodium bicarbonate buffer (pH 8.2) is treated with a solution of dihydroxysuccinimidyl suberate (DSS) in dimethylsulfoxide for 15 minutes at room temperature and then applied to a column of Sephadex G25. The column is eluted with water, and the eluent is monitored by UV spectroscopy. The fractions containing the first peak are combined, frozen as quickly as possible, and lyophilized to dryness. The residue is redissolved in bicarbonate buffer and immediately treated with a solution of serotonin in dimethylsulfoxide for 18 hours at room temperature. The solution is then applied to a Sephadex G25 column which is eluted with water, and the first UV absorbing peak is collected, partially evaporated, and purified by reverse phase C18 HPLC. The later eluting peak is collected and lyophilized to give the serotonin-oligonucleotide conjugate.

EXAMPLE 7

Synthesis of a Poly(hydroxypropyl-methacrylamide)-Oligonucleotide Conjugate

A copolymer of N-(2-hydroxypropyl) methacrylamide and N-methacryloyl-6-aminocaproyl-p-nitrophenyl ester, prepared by the method of Kopecek and Rejmanova in the *Journal of Polymer Science:* Polymer Symposium, Vol. 66, pp. 15–32 (1979) is dissolved in dimethylsulfoxide and added to a solution of a 5'-amino-oligonucleotide in aqueous bicarbonate buffer. The solution is incubated at room temperature for 18 hours, evaporated to remove solvent, and redissolved in water. The solution is centrifuged to remove solid and the supernatant is purified on a reverse phase C18 HPLC column. The late eluting peak is evaporated to dryness to give the poly-HPMA-oligonucleotide conjugate.

EXAMPLE 8

Synthesis of a Dextra-Oligonucleotide Conjugate

A 15-base oligonucleotide was prepared on a DNA synthesizer using standard reagents as supplied by the manufacturer. Cyanoethoxy-di-isopropylamino-trifluoroacetylaminohexyloxy-phosphine (Aminolink II) was used for the final coupling step to introduce a linker arm onto the 5'-terminus of the oligonucleotide. The crude oligonucleotide was treated with concentrated ammonium hydroxide for 12 hours at 55° C. to remove the protecting groups, and the solution was evaporated to dryness. The residue was dissolved in water (0.5 ml) and passed through a Sephadex G25 column which was eluted with water. Fractions were monitored by UV and the first peak to be eluted was evaporated to dryness and dissolved in 0.2 M sodium phosphate buffer pH 8.25. The solution was added to a sample of carboxy-dextran-N-hydroxysuccinimide ester (40 mg) which was prepared by the method of Pietta et al., *Preparative Bochemistry,* Vol. 14, pp. 313–329 (1984). The reactants were stored at room temperature for two days, diluted to 1 ml with water and dialyzed against distilled water for 24 hours at 4° C. using a dialysis membrane with a molecular weight cutoff of 8000. The product was lyophilized, dissolved in 0.1 M triethylammonium acetate buffer pH 7.1 (TEAB), and passed through a Sephadex G25 column (1×30 cm) using TEAB as the eluent. Fractions of 1 ml were collected, and fractions 17–24 were combined and evaporated to dryness. The residue was further purified on a Dionex NucleoPac anion exchange column (4×250 mm) using a gradient of 25 mM tris chloride pH 8 containing 5% acetonitrile as buffer A, and 25 mM tris chloride, 1 M ammonium chloride, pH 8 containing 5% acetonitrile as buffer B. Buffer B was increased from 15% at T=0 to 55% at 15 min. The fractions eluting at 7–9.5 min. were combined and dialyzed against distilled water at 4° C. During this time the water was changed at regular intervals. The product was lyophilized to give the dextran-oligonucleotide conjugate.

It is to be understood, however, that the scope of the present invention is not to be limited to the specific embodiments described above. The invention may be practiced other than as particularly described and still be within the scope of the accompanying claims.

What is claimed is:

1. An oligonucleotide wherein each nucleotide unit of the oligonucleotide includes a sugar moiety, a purine or pyrimidine base, and a phosphorus-containing moiety, wherein said oligonucleotide is conjugated to at least one sugar phosphate moiety which is independent of a nucleotide unit, wherein said at least one sugar phosphate moiety is attached at said purine or pyrimidine base, at said phosphorus-containing moiety, or at said sugar moiety of said oligonucleotide.

2. A composition for binding to an RNA, a DNA, a protein, or a peptide comprising:

(A) an oligonucleotide wherein each nucleotide unit of the oligonucleotide includes a sugar moiety, a purine or pyrimidine base, and a phosphorus-containing moiety wherein said oligonucleotide is conjugated to at least one sugar phosphate moiety which is independent of a nucleotide unit, wherein said at least one sugar phosphate moiety is attached at said purine or pyrimidine base, at said phosphorus-containing moiety, or at said sugar moiety of said nucleotide, and (B) an acceptable pharmaceutical carrier, wherein said oligonucleotide is present in an effective binding amount to an RNA, a DNA, a protein, or a peptide.

3. A probe for determining the presence of a target DAN or RNA sequence, comprising:

an oligonucleotide wherein each nucleotide unit of the oligonucleotide includes a sugar moiety, a purine or pyrimidine base, and a phosphorus-containing moiety, wherein said oligonucleotide is conjugated to at least one sugar phosphate moiety which is independent of a nucleotide unit, wherein said at least one sugar phosphate moiety is attached at said purine or pyrimidine base, at said phosphorus-containing moiety, or at said sugar moiety of said oligonucleotide.

4. The oligonucleotide of claim 1 wherein said sugar phosphate is selected from the group consisting of mannose-6-phosphate, glucose-6-phosphate, galactose-6-phosphate, mannose-1-phosphate, glucose-1-phosphate, galactose-1-phosphate, 6-O-phosphoryl-α-D-mannopyranosyl-(1-2)-D- mannopyranose, 6-O-phosphoryl-α-D-mannopyranosyl-(1-3)-D-mannopyranose, 6-O-phosphoryl-α-D-mannopyranosyl-(1-6)-D-mannopyranose, 6-O-phosphoryl-α-D-mannopyranosyl-(1-2)-D-mannopyranose-(1-2)-D-mannopyranose, and pentamannose-6-phosphate.

5. The oligonucleotide of claim 2 wherein said sugar phosphate is selected from the group consisting of mannose-6-phosphate, glucose-6-phosphate, galactose6-phosphate, mannose-1-phosphate, glucose-1-phosphate, galactose-1-phosphate, 6-O-phosphoryl-α-D-mannopyranosyl-(1-2)-D-mannopyranose, 6-O-phosphoryl-α-D-mannopyranosyl-(1-3)-D-mannopyranose, 6-O-phosphoryl-α-D-mannopyranosyl-(1-6)-D-mannopyranose, 6-O-phosphoryl-α-D-mannopyranosyl-(1-2)-D-mannopyranose-(1-2)-D-mannopyranose, and pentamannose-6-phosphate.

\* \* \* \* \*